(12) United States Patent
Zhang

(10) Patent No.: US 8,226,990 B2
(45) Date of Patent: Jul. 24, 2012

(54) COMPOSITION FOR TREATMENT OF DIABETES MELLITUS AND A PREPARATION AND AN USE THEREOF

(75) Inventor: Xiaoyong Zhang, Zoucheng (CN)

(73) Assignee: Beijing DFJX New Technology Co., Ltd., Beijing (CN)

( * ) Notice: Subject to any disclaimer, the term of this patent is extended or adjusted under 35 U.S.C. 154(b) by 256 days.

(21) Appl. No.: 12/599,451

(22) PCT Filed: Aug. 2, 2007

(86) PCT No.: PCT/CN2007/070409
§ 371 (c)(1),
(2), (4) Date: Nov. 9, 2009

(87) PCT Pub. No.: WO2008/138191
PCT Pub. Date: Nov. 20, 2008

(65) Prior Publication Data
US 2011/0243984 A1     Oct. 6, 2011

(30) Foreign Application Priority Data
May 10, 2007     (CN) .......................... 2007 1 0104381

(51) Int. Cl.
*A61K 36/00* (2006.01)
*A61K 36/77* (2006.01)
*A61K 36/42* (2006.01)
*A61K 36/02* (2006.01)

(52) U.S. Cl. .............. 424/725; 424/195.17; 424/195.18; 424/758

(58) Field of Classification Search .................. None
See application file for complete search history.

(56) References Cited

FOREIGN PATENT DOCUMENTS

| CN | 1135340 A | * | 11/1996 |
| CN | 1146298 A | * | 4/1997 |
| CN | 1234266 A |   | 11/1999 |
| CN | 1287007 A | * | 3/2001 |
| CN | 1579234 A |   | 2/2005 |
| JP | 2007070266 A | * | 3/2007 |

* cited by examiner

*Primary Examiner* — Qiuwen Mi
(74) *Attorney, Agent, or Firm* — Morris Manning & Martin LLP; Tim Tingkang Xia, Esq.

(57) ABSTRACT

The present invention relates to a composition for treating diabetes and a preparation method thereof as well as use thereof. The present invention provides a composition for treating the diabetes, comprising the following active components based on the parts by weight: 10-100 parts of Pumpkin powder; 6-200 parts of spirulina; and 2-90 parts of Lychee Seed. The invention further provides the preparation method of the composition and the use of the medicament for treating the diabetes. By taking the composition, the blood sugar concentration of the diabetics can be effectively controlled, the complicating diseases of the diabetics can be avoided, and the health of the diabetics can be protected.

6 Claims, No Drawings

COMPOSITION FOR TREATMENT OF DIABETES MELLITUS AND A PREPARATION AND AN USE THEREOF

FIELD OF THE INVENTION

The present invention relates to a composition for treating diabetes and a preparation method thereof as well as use thereof.

BACKGROUND

In the past half century, various diabetics have nearly spread around each country and each region in the word. The diabetes is regarded as an internal medicine common disease, which is substantially characterized by persistent hyperglycemia, and the pathogenesis has not been definitely defined around the world currently. The diabetes is not the disease which is cased by single reason and single pathogenesis but the general name of a group of metabolic disease which is caused by inadequate insulin or low insulin effect for different reasons, wherein, the sugar metabolic disturbance is the essential pathologic reaction in the clinic. The diabetes can be generally divided into primary diabetes and secondary diabetes, wherein, the secondary diabetes accounts for about 5% of the diabetes, which is generally named as insulin-dependent diabetes mellitus (IDDM), namely, type I diabetes; and the diabetics has a little or no insulin: insulin injection is necessary to maintain diabetics life, otherwise, the diabetics suffer from the diabetic ketoacidosis and even quickly die. The primary diabetes accounts for about 95% of the diabetes, which is generally named as noninsulin-dependent diabetes mellitus, namely, type II diabetes; the disease onset is slow, and the onset age is after middle age usually but in any age at some times; self-engendered insulin level can normally increase or decrease, or secretion peak is delayed; a bout 60% diabetics is high weight or fat, and has hyperinsulinemia and insulin resistance; and most diabetics orally take hypoglycemic agent to control blood sugar, however, some of the diabetics also need insulin to control blood sugar, in particular to the II diabetics who are not fat. There are more than dozens kinds of medicaments for treating the diabetes from home and abroad at the present, objectively speaking: the effects of the Chinese hypoglycemic agent and the Western hypoglycemic agent for treating the type II diabetes are generally good and basically the same.

SUMMARY OF THE INVENTION

The present invention provides a composition for treating the diabetes, comprising the following active components based on the parts by weight:
10-100 parts of Pumpkin powder;
6-200 parts of spirulina; and
2-90 parts of Lychee Seed.
Preferably, the composition further comprises 10-100 parts of balsam pear powder.
Preferably, the composition comprises the following active components based on the parts by weight:
10-60 parts of Pumpkin powder;
6-80 parts of spirulina;
2-60 parts of Lychee Seed; and
10-60 parts of balsam pear powder.
The invention further provides a method for preparing the composition, comprising steps of grinding and mixing the active components.

The invention further relates to use of the medicament for treating the diabetes.
The invention realizes the technical effects as follows:
By taking the composition, the blood sugar concentration of the diabetics can be effectively controlled, the complicating diseases of the diabetics can be avoided, and the health of the diabetics can be protected.

DETAILED DESCRIPTION OF THE INVENTION

EXAMPLE 1

Firstly, the fresh pumpkin which is planted in accordance with the standard plant soil, plant water source and plant environment for planting green products and is free of any three wastes pollution source is cut into flakiness with equal size by a cutting tool, is naturally cooled under sterile circumstances and is dried into dried pumpkin after being normally processed; the dried pumpkin is cut into small pieces with size of about 1.5*1.5 cm; the small pieces are dried in a sterilizing way to have standard colour and lustre with a high-temperature sterilizing drier under the standard sterilizing and drying temperature; the dried pumpkin is naturally cooled in sterile space; the dried pumpkin is sterilized with a sterile grinder into small pieces with size of about 1 cm*1.5 cm; and the small pieces are processed into pumpkin fine powder with size of Phi 0.2 mm to be spare by a professional procedure and device. Secondly, the fresh balsam pear which is planted in accordance with the standard plant soil, plant water source and plant environment for planting green products and is free of any three wastes pollution source is cut into flakiness with equal size by a cutting tool, is naturally cooled under the sterile circumstances and is dried into dried balsam pear after being normally processed; the dried balsam pear is cut into small pieces with size of about 1.2*1.5 cm; the balsam pear is dried in a sterilizing way to have standard colour and lustre with a high-temperature sterilizing drier under the standard sterilizing and drying temperature; the dried balsam pear is naturally cooled in sterile space; the dried balsam pear is sterilized with a sterile grinder into small pieces with size of about 1.5*1.5 cm; and the small pieces are processed into balsam pear fine powder with size of Phi 0.1 mm to be spare in a combination way by a professional procedure and device. Thirdly, the natural spirulina which is processed in a way of standard sterilization is processed into gain powder with size of Phi 0.1 mm to be spare in a combination way by the same sterile fine grinder; and the spirulina which is processed in a way of standard sterilization is processed into gain powder with size of Phi 0.1 mm so as to be spare in a combination way by the same sterile fine grinder. Finally, the skin and the flesh of the fresh lychee is skinned to remain the seed, the seed is dried by a standard sterilizing device and grinded into grains with size of Phi 0.5 cm, and the dried seed is processed into lychee seed fine powder with size of Phi 0.15 mm to be spare in a combination way according to different dosages after being processed in a way of standard sterilization.

EXAMPLE 2

Aiming at the levis diabetics in the type II diabetics, the dosage and the taking mode of breakfast on an empty stomach at every morning are prepared by dosing the powdery pumpkin fine powder, the balsam pear fine powder, the spirulina fine powder and the lychee seed fine powder which are prepared by the example 1 under sterile environment in the follows ways:

1. Adding the spirulina fine powder 8 mg and the lychee seed fine powder 2 mg into the pumpkin fine powder 14 g to form type A breakfast for the levis diabetics in the type II diabetics, namely, preparing into soupy breakfast for food therapy on an empty stomach with 150 ml boiled water under 80 DEG. C. 20 minutes before breakfast;
2. Adding the spirulina fine powder 10 mg and the lychee seed fine powder 3 mg into the pumpkin fine powder 14.5 g to form type B breakfast for the levis diabetics in the type II diabetics, namely, preparing into soupy breakfast for food therapy on an empty stomach with 150 ml boiled water under 80 DEG. C. 20 minutes before breakfast;
3. Adding the spirulina fine powder 12 mg and the lychee seed fine powder 4 mg into the pumpkin fine powder 15 g to form type C breakfast for the levis diabetics in the type II diabetics, namely, preparing into soupy breakfast for food therapy on an empty stomach with 150 ml boiled water under 80 DEG. C. 20 minutes before breakfast;
4. Adding the spirulina fine powder 14 mg and the lychee seed fine powder 5 mg into the pumpkin fine powder 15.5 g to form type D breakfast for the levis diabetics in the type II diabetics, namely, preparing into soupy breakfast for food therapy on an empty stomach with 150 ml boiled water under 80 DEG. C. 20 minutes before breakfast;
5. Adding the spirulina fine powder 16 mg and the lychee seed fine powder 6 mg into the pumpkin fine powder 16 g to form type H breakfast for the levis diabetics in the type II diabetics, namely, preparing into soupy breakfast for food therapy on an empty stomach with 150 ml boiled water under 80 DEG. C. 20 minutes before breakfast;
6. Adding the spirulina fine powder 18 mg and the lychee seed fine powder 7 mg into the pumpkin fine powder 16.5 g to form type F breakfast for the levis diabetics in the type II diabetics, namely, preparing into soupy breakfast for food therapy on an empty stomach with 150 ml boiled water under 80 DEG. C. 20 minutes before breakfast;
7. Adding the spirulina fine powder 20 mg and the lychee seed fine powder 8 mg into the pumpkin fine powder 17 g to form type G breakfast for the levis diabetics in the type II diabetics, namely, preparing into soupy breakfast for food therapy on an empty stomach with 150 ml boiled water under 80 DEG. C. 20 minutes before breakfast;
8. Adding the spirulina fine powder 20 mg and the lychee seed fine powder 9 mg into the pumpkin fine powder 17.2 g to form type H breakfast for the levis diabetics in the type II diabetics, namely, preparing into soupy breakfast for food therapy on an empty stomach with 150 ml boiled water under 80 DEG. C. 20 minutes before breakfast;
9. Adding the spirulina fine powder 20 mg and the lychee seed fine powder 10 mg into the pumpkin fine powder 17.4 g to form type J breakfast for the levis diabetics in the type II diabetics, namely, preparing into soupy breakfast for food therapy on an empty stomach with 150 ml boiled water under 80 DEG. C. 20 minutes before breakfast;

EXAMPLE 3

Aiming at the middle diabetics in the type II diabetics, the dosage and the taking mode of breakfast on an empty stomach at every morning are prepared by dosing the powdery pumpkin fine powder, the spirulina fine powder and the lychee seed fine powder which are prepared by the example 1 under sterile environment in the follows ways:
1. Adding the spirulina fine powder 22 mg and the lychee seed fine powder 12 mg into the pumpkin fine powder 17.5 g to form type A breakfast for the middle diabetics in the type II diabetics, namely, preparing into soupy breakfast for food therapy on an empty stomach with 150 ml boiled water under 80 DEG. C. 20 minutes before breakfast;
2. Adding the spirulina fine powder 24 mg and the lychee seed fine powder 13 mg into the pumpkin fine powder 18 g to form type B breakfast for the middle diabetics in the type II diabetics, namely, preparing into soupy breakfast for food therapy on an empty stomach with 150 ml boiled water under 80 DEG. C. 20 minutes before breakfast;
3. Adding the spirulina fine powder 26 mg and the lychee seed fine powder 14 mg into the pumpkin fine powder 18.5 g to form type C breakfast for the middle diabetics in the type II diabetics, namely, preparing into soupy breakfast for food therapy on an empty stomach with 150 ml boiled water under 80 DEG. C. 20 minutes before breakfast;
4. Adding the spirulina fine powder 28 mg and the lychee seed fine powder 15 mg into the pumpkin fine powder 19 g to form type D breakfast for the middle diabetics in the type II diabetics, namely, preparing into soupy breakfast for food therapy on an empty stomach with 150 ml boiled water under 80 DEG. C. 20 minutes before breakfast;
5. Adding the spirulina fine powder 30 mg and the lychee seed fine powder 16 mg into the pumpkin fine powder 19.5 g to form type E breakfast for the middle diabetics in the type II diabetics, namely, preparing into soupy breakfast for food therapy on an empty stomach with 150 ml boiled water under 80 DEG. C. 20 minutes before breakfast;
6. Adding the spirulina fine powder 32 mg and the lychee seed fine powder 17 mg into the pumpkin fine powder 20 g to form type F breakfast for the middle diabetics in the type II diabetics, namely, preparing into soupy breakfast for food therapy on an empty stomach with 150 ml boiled water under 80 DEG. C. 20 minutes before breakfast;
7. Adding the spirulina fine powder 34 mg and the lychee seed fine powder 18 mg into the pumpkin fine powder 20.5 g to form type G breakfast for the middle diabetics in the type II diabetics, namely, preparing into soupy breakfast for food therapy on an empty stomach with 150 ml boiled water under 80 DEG. C. 20 minutes before breakfast.
8. Adding the spirulina fine powder 34.5 mg and the lychee seed fine powder 19 mg into the pumpkin fine powder 20.7 g to form type H breakfast for the middle diabetics in the type II diabetics, namely, preparing into soupy breakfast for food therapy on an empty stomach with 150 ml boiled water under 80 DEG. C. 20 minutes before breakfast;
9. Adding the spirulina fine powder 35 mg and the lychee seed fine powder 20 mg into the pumpkin fine powder 20.9 g to form type J breakfast for the middle diabetics in the type II diabetics, namely, preparing into soupy breakfast for food therapy on an empty stomach with 150 ml boiled water under 80 DEG. C. 20 minutes before breakfast;

EXAMPLE 4

Aiming at the severe diabetics in the type II diabetics, the dosage and the taking mode of breakfast on an empty stomach at every morning are prepared by dosing the powdery pumpkin fine powder, the spirulina fine powder and the lychee seed fine powder which are prepared by the example 1 under sterile environment in the follows ways:
1. Adding the spirulina fine powder 36 mg and the lychee seed fine powder 21 mg into the pumpkin fine powder 21 g to form type A breakfast for the severe diabetics in the type II diabetics, namely, preparing into soupy breakfast for food therapy on an empty stomach with 150 ml boiled water under 90 DEG. C. 20 minutes before breakfast;
2. Adding the spirulina fine powder 38 mg and the lychee seed fine powder 21 mg into the pumpkin fine powder 21.5 g to form type B breakfast for the severe diabetics in the type II diabetics, namely, preparing into soupy breakfast for food therapy on an empty stomach with 150 ml boiled water under 90 DEG. C. 20 minutes before breakfast;
3. Adding the spirulina fine powder 40 mg and the lychee seed fine powder 22 mg into the pumpkin fine powder 22 g to form type C breakfast for the severe diabetics in the type II diabetics, namely, preparing into soupy breakfast for food therapy on an empty stomach with 150 ml boiled water under 90 DEG. C. 20 minutes before breakfast;
4. Adding the spirulina fine powder 42 mg and the lychee seed fine powder 22.5 mg into the pumpkin fine powder 22.5 g to form type D breakfast for the severe diabetics in the type II diabetics, namely, preparing into soupy breakfast for food therapy on an empty stomach with 150 ml boiled water under 90 DEG. C. 20 minutes before breakfast;
5. Adding the spirulina fine powder 44 mg and the lychee seed fine powder 21 mg into the pumpkin fine powder 23 g to form type E breakfast for the severe diabetics in the type II diabetics, namely, preparing into soupy breakfast for food therapy on an empty stomach with 150 ml boiled water under 90 DEG. C. 20 minutes before breakfast;
6. Adding the spirulina fine powder 46 mg and the lychee seed fine powder 24 mg into the pumpkin fine powder 23.5 g to form type F breakfast for the severe diabetics in the type II diabetics, namely, preparing into soupy breakfast for food therapy on an empty stomach with 150 ml boiled water under 90 DEG. C. 20 minutes before breakfast;
7. Adding the spirulina fine powder 48 mg and the lychee seed fine powder 27 mg into the pumpkin fine powder 24 g to form type G breakfast for the severe diabetics in the type II diabetics, namely, preparing into soupy breakfast for food therapy on an empty stomach with 150 ml boiled water under 90 DEG. C. 20 minutes before breakfast.
8. Adding the spirulina fine powder 48.2 mg and the lychee seed fine powder 30 mg into the pumpkin fine powder 24.2 g to form type H breakfast for the severe diabetics in the type II diabetics, namely, preparing into soupy breakfast for food therapy on an empty stomach with 150 ml boiled water under 90 DEG. C. 20 minutes before breakfast;
9. Adding the spirulina fine powder 48.5 mg and the lychee seed fine powder 33 mg into the pumpkin fine powder 24.4 g to form type J breakfast for the severe diabetics in the type II diabetics, namely, preparing into soupy breakfast for food therapy on an empty stomach with 150 ml boiled water under 90 DEG. C. 20 minutes before breakfast;

EXAMPLE 5

Aiming at the levis diabetics in the type II diabetics, the preparation, the dosage and the taking mode of snacks for balancing non-fasting blood sugar at every morning are prepared by dosing the prepared lychee seed fine powder, the spirulina fine powder and the balsam pear fine powder under sterile environment in the follows ways:
1. Adding the spirulina fine powder 15 mg and the balsam pear fine powder 3 g into the lychee seed fine powder 2.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type A breakfast, the lunch and the dinner with warm water under 60 DEG. C.;
2. Adding the spirulina fine powder 25 mg and the balsam pear fine powder 3.5 g into the lychee seed fine powder 3.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type B breakfast, the lunch and the dinner with warm water under 60 DEG. C.;
3. Adding the spirulina fine powder 35 mg and the balsam pear fine powder 4 g into the lychee seed fine powder 4.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type C breakfast, the lunch and the dinner with warm water under 60 DEG. C.;
4. Adding the spirulina fine powder 45 mg and the balsam pear fine powder 4.5 g into the lychee seed fine powder 5.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type D breakfast, the lunch and the dinner with warm water under 60 DEG. C;.
5. Adding the spirulina fine powder 55 mg and the balsam pear fine powder 5 g into the lychee seed fine powder 6.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type E breakfast, the lunch and the dinner with warm water under 60 DEG. C.;
6. Adding the spirulina fine powder 65 mg and the balsam pear fine powder 5.5 g into the lychee seed fine powder 7.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type F breakfast, the lunch and the dinner with warm water under 60 DEG. C..
7. Adding the spirulina fine powder 75 mg and the balsam pear fine powder 6 g into the lychee seed fine powder 8.5 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type G breakfast, the lunch and the dinner with warm water under 60 DEG. C.;
8. Adding the spirulina fine powder 77 mg and the balsam pear fine powder 6.5 g into the lychee seed fine powder 8.7 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type H breakfast, the lunch and the dinner with warm water under 60 DEG. C.;
9. Adding the spirulina fine powder 79 mg and the balsam pear fine powder 6.9 g into the lychee seed fine powder 8.9 g, and evenly mixing the mixture to form 1 g/piece troche or 0.5-1 g/gian capsule, namely, forming the snacks for balancing non-fasting blood sugar for the levis diabetics in the type II diabetics, wherein, the snacks are taken 5 minutes within the type J breakfast, the lunch and the dinner with warm water under 60 DEG. C.;

EXAMPLE 6

Aiming at the middle diabetics in the type II diabetics, the preparation, the dosage and the taking mode of snacks for balancing non-fasting blood sugar at every morning are prepared by dosing the prepared lychee seed fine powder, the spirulina fine powder and the balsam pear fine powder under sterile environment in the follows ways:

1. Adding the spirulina fine powder 25 mg and the balsam pear fine powder 4 g into the lychee seed fine powder 9.5 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type A breakfast, the lunch and the dinner with warm water under 60 DEG. C.DEG C.;
2. Adding the spirulina fine powder 35 mg and the balsam pear fine powder 4.5 g into the lychee seed fine powder 9.7 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type B breakfast, the lunch and the dinner with warm water under 60 DEG. C.;
3. Adding the spirulina fine powder 45 mg and the balsam pear fine powder 5 g into the lychee seed fine powder 9.9 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type C breakfast, the lunch and the dinner with warm water under 60 DEG. C.;
4. Adding the spirulina fine powder 55 mg and the balsam pear fine powder 5.5 g into the lychee seed fine powder 10.1 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type D breakfast, the lunch and the dinner with warm water under 60 DEG. C.;
5. Adding the spirulina fine powder 65 mg and the balsam pear fine powder 6 g into the lychee seed fine powder 10.3 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type E breakfast, the lunch and the dinner with warm water under 60 DEG. C.;
6. Adding the spirulina fine powder 75 mg and the balsam pear fine powder 6.5 g into the lychee seed fine powder 10.5 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type F breakfast, the lunch and the dinner with warm water under 60 DEG. C.;
7. Adding the spirulina fine powder 85 mg and the balsam pear fine powder 7 g into the lychee seed fine powder 10.7 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type G breakfast, the lunch and the dinner with warm water under 60 DEG. C.;
8. Adding the spirulina fine powder 87 mg and the balsam pear fine powder 7.5 g into the lychee seed fine powder 10.9 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type H breakfast, the lunch and the dinner with warm water under 60 DEG. C.;.
9. Adding the spirulina fine powder 89 mg and the balsam pear fine powder 7.9 g into the lychee seed fine powder 11.19 g, and evenly mixing the mixture to form 1 g/piece troche or 0.5-1 g/gian capsule, namely, forming the snacks for balancing non-fasting blood sugar for the middle diabetics in the type II diabetics, wherein, the snacks are taken 5 minutes within the type J breakfast, the lunch and the dinner with warm water under 60 DEG. C.;

EXAMPLE 7

Aiming at the severe diabetics in the type II diabetics, the preparation, the dosage and the taking mode of snacks for balancing non-fasting blood sugar at every morning are prepared by dosing the prepared lychee seed fine powder, the spirulina fine powder and the balsam pear fine powder under sterile environment in the follows ways:

1. Adding the spirulina fine powder 35 mg and the balsam pear fine powder 5 g into the lychee seed fine powder 11.3 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type A breakfast, the lunch and the dinner with warm water under 60 DEG. C.;
2. Adding the spirulina fine powder 45 mg and the balsam pear fine powder 5.5 g into the lychee seed fine powder 11.5 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type B breakfast, the lunch and the dinner with warm water under 60 DEG. C.;
3. Adding the spirulina fine powder 55 mg and the balsam pear fine powder 6 g into the lychee seed fine powder 11.3 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type C breakfast, the lunch and the dinner with warm water under 60 DEG. C.;
4. Adding the spirulina fine powder 65 mg and the balsam pear fine powder 6.5 g into the lychee seed fine powder 11.9 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type D breakfast, the lunch and the dinner with warm water under 60 DEG. C.;
5. Adding the spirulina fine powder 75 mg and the balsam pear fine powder 7 g into the lychee seed fine powder 12.1 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type E breakfast, the lunch and the dinner with warm water under 60 DEG. C.;
6. Adding the spirulina fine powder 85 mg and the balsam pear fine powder 7.5 g into the lychee seed fine powder 12.3 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type F breakfast, the lunch and the dinner with warm water under 60 DEG. C.;
7. Adding the spirulina fine powder 95 mg and the balsam pear fine powder 8 g into the lychee seed fine powder 12.5 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type G breakfast, the lunch and the dinner with warm water under 60 DEG. C.;

8. Adding the spirulina fine powder 97 mg and the balsam pear fine powder 8.5 g into the lychee seed fine powder 12.7 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type A breakfast, the lunch and the dinner with warm water under 60 DEG. C.;.

9. Adding the spirulina fine powder 99 mg and the balsam pear fine powder 8.9 g into the lychee seed fine powder 12.9 g, and evenly mixing the mixture to form 1 g/piece troche or 0.5-1 g/gian capsule, namely, forming the snacks for balancing non-fasting blood sugar for the severe diabetics in the type II diabetics, wherein, the snacks are taken 5 minutes within the type J breakfast, the lunch and the dinner with warm water under 60 DEG. C.;

EXAMPLE 8

Aiming at the levis diabetics in the type II diabetics, the preparation, the dosage and the taking mode of special snacks which are eaten between the breakfast and the lunch, between the lunch and the dinner as well as 30 minutes before sleep are prepared by dosing the qualifiedly prepared spirulina fine powder, the pumpkin fine powder and the lychee seed fine powder under absolute sterile environment in the follows ways:

1. Adding the pumpkin fine powder 6 g and the lychee seed fine powder 5 mg into the spirulina fine powder 0.5 g, and evenly mixing the mixture to form the snacks with weight of 6.5005 g/piece, namely, forming the snacks which are eaten among the type A breakfast, lunch and dinner in 2-3 hours for the levis diabetics in the type II diabetics when the diabetics are hungry;
2. Adding the pumpkin fine powder 6.5 g and the lychee seed fine powder 6 mg into the spirulina fine powder 0.8 g, and evenly mixing the mixture to form the snacks with weight of 7.3006 g/piece, namely, forming the snacks which are eaten among the type B breakfast, lunch and dinner in 2-3 hours for the levis diabetics in the type II diabetics when the diabetics are hungry;
3. Adding the pumpkin fine powder 7 g and the lychee seed fine powder 7 mg into the spirulina fine powder 1.1 g, and evenly mixing the mixture to form the snacks with weight of 8.1007 g/piece, namely, forming the snacks which are eaten among the type C breakfast, lunch and dinner in 2-3 hours for the levis diabetics in the type II diabetics when the diabetics are hungry;
4. Adding the pumpkin fine powder 7.5 g and the lychee seed fine powder 8 mg into the spirulina fine powder 1.4 g, and evenly mixing the mixture to form the snacks with weight of 8.9008 g/piece, namely, forming the snacks which are eaten among the type D breakfast, lunch and dinner in 2-3 hours for the levis diabetics in the type II diabetics when the diabetics are hungry;
5. Adding the pumpkin fine powder 8 g and the lychee seed fine powder 9 mg into the spirulina fine powder 1.7 g, and evenly mixing the mixture to form the snacks with weight of 9.7009 g/piece, namely, forming the snacks which are eaten among the type C breakfast, lunch and dinner in 2-3 hours for the levis diabetics in the type II diabetics when the diabetics are hungry;
6. Adding the pumpkin fine powder 8.510.501 g and the lychee seed fine powder 10 mg into the spirulina fine powder 2 g, and evenly mixing the mixture to form the snacks with weight of 16.001 g/piece, namely, forming the snacks which are eaten among the type F breakfast, lunch and dinner in 2-3 hours for the levis diabetics in the type II diabetics when the diabetics are hungry;
7. Adding the pumpkin fine powder 9 g and the lychee seed fine powder 11 mg into the spirulina fine powder 2.3 g, and evenly mixing the mixture to form the snacks with weight of 11.3011 g/piece, namely, forming the snacks which are eaten among the type G breakfast, lunch and dinner in 2-3 hours for the levis diabetics in the type II diabetics when the diabetics are hungry;
8. Adding the pumpkin fine powder 9.5 g and the lychee seed fine powder 11.4 mg into the spirulina fine powder 2.5 g, and evenly mixing the mixture to form the snacks with weight of 12.0114 g/piece, namely, forming the snacks which are eaten among the type H breakfast, lunch and dinner in 2-3 hours for the levis diabetics in the type II diabetics when the diabetics are hungry;
9. Adding the pumpkin fine powder 9.9 g and the lychee seed fine powder 11.9 mg into the spirulina fine powder 2.7 g, and evenly mixing the mixture to form the snacks with weight of 12.6119 g/piece, namely, forming the snacks which are eaten among the type J breakfast, lunch and dinner in 2-3 hours for the levis diabetics in the type II diabetics when the diabetics are hungry;

EXAMPLE 9

Aiming at the middle diabetics in the type II diabetics, the preparation, the dosage and the taking mode of special snacks which are eaten between the breakfast and the lunch, between the lunch and the dinner as well as 30 minutes before sleep are prepared by dosing the qualifiedly prepared spirulina fine powder, the pumpkin fine powder and the lychee seed fine powder under absolute sterile environment in the follows ways:

1. Adding the pumpkin fine powder 9.5 g and the lychee seed fine powder 12 mg into the spirulina fine powder 2.6 g, and evenly mixing the mixture to form the snacks with weight of 12.1012 g/piece, namely, forming the snacks which are eaten among the type A breakfast, lunch and dinner in 2-3 hours for the middle diabetics in the type II diabetics when the diabetics are hungry;
2. Adding the pumpkin fine powder 10 g and the lychee seed fine powder 13 mg into the spirulina fine powder 2.9 g, and evenly mixing the mixture to form the snacks with weight of 12.9013 g/piece, namely, forming the snacks which are eaten among the type B breakfast, lunch and dinner in 2-3 hours for the middle diabetics in the type II diabetics when the diabetics are hungry;
3. Adding the pumpkin fine powder 9.5 g and the lychee seed fine powder 12 mg into the spirulina fine powder 2.6 g, and evenly mixing the mixture to form the snacks with weight of 12.1012 g/piece, namely, forming the snacks which are eaten among the type C breakfast, lunch and dinner in 2-3 hours for the middle diabetics in the type II diabetics when the diabetics are hungry;
4. Adding the pumpkin fine powder 11 g and the lychee seed fine powder 15 mg into the spirulina fine powder 3.5 g, and evenly mixing the mixture to form the snacks with weight of 14.5015 g/piece, namely, forming the snacks which are eaten among the type D breakfast, lunch and dinner in 2-3 hours for the middle diabetics in the type II diabetics when the diabetics are hungry;
5. Adding the pumpkin fine powder 11.5 g and the lychee seed fine powder 16 mg into the spirulina fine powder 3.8 g, and evenly mixing the mixture to form the snacks with weight of 14.3016 g/piece, namely, forming the snacks which are eaten among the type E breakfast, lunch and dinner in 2-3 hours for the middle diabetics in the type II diabetics when the diabetics are hungry;
6. Adding the pumpkin fine powder 12 g and the lychee seed fine powder 17 mg into the spirulina fine powder 4.1 g, and evenly mixing the mixture to form the snacks with weight of 16.1017 g/piece, namely, forming the snacks which are eaten among the type F breakfast, lunch and dinner in 2-3 hours for the middle diabetics in the type II diabetics when the diabetics are hungry;
7. Adding the pumpkin fine powder 12.5 g and the lychee seed fine powder 18 mg into the spirulina fine powder 4.4 g, and evenly mixing the mixture to form the snacks with weight of 16.9018 g/piece, namely, forming the snacks which are eaten among the type G breakfast, lunch and dinner in 2-3 hours for the middle diabetics in the type II diabetics when the diabetics are hungry;
8. Adding the pumpkin fine powder 12.7 g and the lychee seed fine powder 18.4 mg into the spirulina fine powder 4.6 g, and evenly mixing the mixture to form the snacks with weight of 12.7 g/piece, namely, forming the snacks which are eaten among the type H breakfast, lunch and dinner in 2-3 hours for the middle diabetics in the type II diabetics when the diabetics are hungry;
9. Adding the pumpkin fine powder 12.9 g and the lychee seed fine powder 18.8 mg into the spirulina fine powder 4.8 g, and evenly mixing the mixture to form the snacks with weight of 17.7188 g/piece, namely, forming the snacks which are eaten among the type G breakfast, lunch and dinner in 2-3 hours for the middle diabetics in the type II diabetics when the diabetics are hungry;

EXAMPLE 10

Aiming at the severe diabetics in the type II diabetics, the preparation, the dosage and the taking mode of special snacks which are eaten between the breakfast and the lunch, between the lunch and the dinner as well as 30 minutes before sleep are prepared by dosing the qualifiedly prepared spirulina fine powder, the pumpkin fine powder and the lychee seed fine powder under absolute sterile environment in the follows ways:
1. Adding the pumpkin fine powder 13 g and the lychee seed fine powder 19 mg into the spirulina fine powder 4.5 g, and evenly mixing the mixture to form the snacks with weight of 17.5019 g/piece, namely, forming the snacks which are eaten among the type A breakfast, lunch and dinner in 2-3 hours for the levis diabetics in the type II diabetics when the diabetics are hungry;
2. Adding the pumpkin fine powder 13.5 g and the lychee seed fine powder 20 mg into the spirulina fine powder 4.6 g, and evenly mixing the mixture to form the snacks with weight of 18.102 g/piece, namely, forming the snacks which are eaten among the type B breakfast, lunch and dinner in 2-3 hours for the levis diabetics in the type II diabetics when the diabetics are hungry;
3. Adding the pumpkin fine powder 14 g and the lychee seed fine powder 21 mg into the spirulina fine powder 4.7 g, and evenly mixing the mixture to form the snacks with weight of 18.7021 g/piece, namely, forming the snacks which are eaten among the type C breakfast, lunch and dinner in 2-3 hours for the levis diabetics in the type II diabetics when the diabetics are hungry;
4. Adding the pumpkin fine powder 14.5 g and the lychee seed fine powder 22 mg into the spirulina fine powder 4.8 g, and evenly mixing the mixture to form the snacks with weight of 18.3022 g/piece, namely, forming the snacks which are eaten among the type D breakfast, lunch and dinner in 2-3 hours for the levis diabetics in the type II diabetics when the diabetics are hungry;
5. Adding the pumpkin fine powder 15 g and the lychee seed fine powder 23 mg into the spirulina fine powder 4.9 g, and evenly mixing the mixture to form the snacks with weight of 19.9023 g/piece, namely, forming the snacks which are eaten among the type E breakfast, lunch and dinner in 2-3 hours for the levis diabetics in the type II diabetics when the diabetics are hungry;
6. Adding the pumpkin fine powder 15.5 g and the lychee seed fine powder 24 mg into the spirulina fine powder 5 g, and evenly mixing the mixture to form the snacks with weight of 20.5024 g/piece, namely, forming the snacks which are eaten among the type F breakfast, lunch and dinner in 2-3 hours for the levis diabetics in the type II diabetics when the diabetics are hungry;
7. Adding the pumpkin fine powder 16 g and the lychee seed fine powder 25 mg into the spirulina fine powder 4.5 g, and evenly mixing the mixture to form the snacks with weight of 21.1025 g/piece, namely, forming the snacks which are eaten among the type G breakfast, lunch and dinner in 2-3 hours for the levis diabetics in the type II diabetics when the diabetics are hungry;
8. Adding the pumpkin fine powder 16.5 g and the lychee seed fine powder 26 mg into the spirulina fine powder 5.25 g, and evenly mixing the mixture to form the snacks with weight of 21.7026 g/piece, namely, forming the snacks which are eaten among the type H breakfast, lunch and dinner in 2-3 hours for the levis diabetics in the type II diabetics when the diabetics are hungry;
9. Adding the pumpkin fine powder 17 g and the lychee seed fine powder 27 mg into the spirulina fine powder 5.3 g, and evenly mixing the mixture to form the snacks with weight of 22.3027 g/piece, namely, forming the snacks which are eaten among the type J breakfast, lunch and dinner in 2-3 hours for the levis diabetics in the type II diabetics when the diabetics are hungry;

EXAMPLE 11

Aiming at the levis diabetics in the type II diabetics, the preparation, the dosage and the taking mode of special snacks which have to be eaten before sleep for balancing night blood sugar are prepared by dosing the qualifiedly prepared standard spirulina fine powder, the pumpkin fine powder, the balsam pear fine powder and the lychee seed fine powder under absolute sterile environment in the follows ways:
1. Adding the pumpkin fine powder 2.5 g, the balsam pear fine powder 2 mg and the lychee seed fine powder 2 mg into the spirulina fine powder 1.5 g, and evenly mixing the mixture to form *4 grains with equal weight, namely, forming the snacks which are eaten after the type A dinner and 10 minutes before sleep for the levis diabetics in the type II diabetics, wherein, the snacks have to be eaten at one time for non-fasting food therapy before the sleep with warmer water under 60 DEG. C.;
2. Adding the pumpkin fine powder 3.0 g, the balsam pear fine powder 4 mg and the lychee seed fine powder 2 mg into the spirulina fine powder 2.0 g, and evenly mixing the mixture to form *4 grains with equal weight, namely, forming the snacks which are eaten after the type B dinner and 10 minutes before sleep for the levis diabetics in the type II diabetics, wherein, the snacks have to be eaten at one time for non-fasting food therapy before the sleep with warmer water under 60 DEG. C.;

3. Adding the pumpkin fine powder 3.5 g, the balsam pear fine powder 6 mg and the lychee seed fine powder 2 mg into the spirulina fine powder 2.5 g, and evenly mixing the mixture to form *4 grains with equal weight, namely, forming the snacks which are eaten after the type C dinner and 10 minutes before sleep for the levis diabetics in the type II diabetics, wherein, the snacks have to be eaten at one time for non-fasting food therapy before the sleep with warmer water under 60 DEG. C.;

4. Adding the pumpkin fine powder 4.0 g, the balsam pear fine powder 8 mg and the lychee seed fine powder 2 mg into the spirulina fine powder 3.0 g, and evenly mixing the mixture to form *4 grains with equal weight, namely, forming the snacks which are eaten after the type D dinner and 10 minutes before sleep for the levis diabetics in the type II diabetics, wherein, the snacks have to be eaten at one time for non-fasting food therapy before the sleep with warmer water under 60 DEG. C.;

5. Adding the pumpkin fine powder 4.5 g, the balsam pear fine powder 10 mg and the lychee seed fine powder 2 mg into the spirulina fine powder 3.5 g, and evenly mixing the mixture to form *4 grains with equal weight, namely, forming the snacks which are eaten after the type E dinner and 10 minutes before sleep for the levis diabetics in the type II diabetics, wherein, the snacks have to be eaten at one time for non-fasting food therapy before the sleep with warmer water under 60 DEG. C.;

6. Adding the pumpkin fine powder 5.0 g, the balsam pear fine powder 12 mg and the lychee seed fine powder 2 mg into the spirulina fine powder 4.0 g, and evenly mixing the mixture to form *4 grains with equal weight, namely, forming the snacks which are eaten after the type F dinner and 10 minutes before sleep for the levis diabetics in the type II diabetics, wherein, the snacks have to be eaten at one time for non-fasting food therapy before the sleep with warmer water under 60 DEG. C.;

7. Adding the pumpkin fine powder 5.5 g, the balsam pear fine powder 14 mg and the lychee seed fine powder 2 mg into the spirulina fine powder 4.5 g, and evenly mixing the mixture to form *4 grains with equal weight, namely, forming the snacks which are eaten after the type G dinner and 10 minutes before sleep for the levis diabetics in the type II diabetics, wherein, the snacks have to be eaten at one time for non-fasting food therapy before the sleep with warmer water under 60 DEG. C.;

8. Adding the pumpkin fine powder 5.5 g, the balsam pear fine powder 15 mg and the lychee seed fine powder 2 mg into the spirulina fine powder 4.7 g, and evenly mixing the mixture to form *4 grains with equal weight, namely, forming the snacks which are eaten after the type G dinner and 10 minutes before sleep for the levis diabetics in the type II diabetics, wherein, the snacks have to be eaten at one time for non-fasting food therapy before the sleep with warmer water under 60 DEG. C.;

9. Adding the pumpkin fine powder 5.5 g, the balsam pear fine powder 16 mg and the lychee seed fine powder 2 mg into the spirulina fine powder 4.9 g, and evenly mixing the mixture to form *4 grains with equal weight, namely, forming the snacks which are eaten after the type J dinner and 10 minutes before sleep for the levis diabetics in the type II diabetics, wherein, the snacks have to be eaten at one time for non-fasting food therapy before the sleep with warmer water under 60 DEG. C.;

EXAMPLE 12

Aiming at the middle diabetics in the type II diabetics, the preparation, the dosage and the taking mode of special snacks which have to be eaten before sleep for balancing night blood sugar are prepared by dosing the qualifiedly prepared standard spirulina fine powder, the pumpkin fine powder, the balsam pear fine powder and the lychee seed fine powder under absolute sterile environment in the follows ways:

1. Adding the pumpkin fine powder 3.5 g, the balsam pear fine powder 14.1 mg and the lychee seed fine powder 2 mg into the spirulina fine powder 5 g, and evenly mixing the mixture to form *5 grains with equal weight, namely, forming the snacks which are eaten after the type A dinner and 10 minutes before sleep for the middle diabetics in the type II diabetics, wherein, the snacks have to be eaten at one time for non-fasting food therapy before the sleep with warmer water under 60 DEG. C.;

2. Adding the pumpkin fine powder 4.0 g, the balsam pear fine powder 14.2 mg and the lychee seed fine powder 2 mg into the spirulina fine powder 5.1 g, and evenly mixing the mixture to form *5 grains with equal weight, namely, forming the snacks which are eaten after the type B dinner and 10 minutes before sleep for the middle diabetics in the type II diabetics, wherein, the snacks have to be eaten at one time for non-fasting food therapy before the sleep with warmer water under 60 DEG. C.;

3. Adding the pumpkin fine powder 5.5 g, the balsam pear fine powder 14.3 mg and the lychee seed fine powder 2 mg into the spirulina fine powder 5.3 g, and evenly mixing the mixture to form *5 grains with equal weight, namely, forming the snacks which are eaten after the type C dinner and 10 minutes before sleep for the middle diabetics in the type II diabetics, wherein, the snacks have to be eaten at one time for non-fasting food therapy before the sleep with warmer water under 60 DEG. C.;

4. Adding the pumpkin fine powder 6.0 g, the balsam pear fine powder 14.4 mg and the lychee seed fine powder 2 mg into the spirulina fine powder 5.5 g, and evenly mixing the mixture to form *5 grains with equal weight, namely, forming the snacks which are eaten after the type D dinner and 10 minutes before sleep for the middle diabetics in the type II diabetics, wherein, the snacks have to be eaten at one time for non-fasting food therapy before the sleep with warmer water under 60 DEG. C.;

5. Adding the pumpkin fine powder 7.5 g, the balsam pear fine powder 14.5 mg and the lychee seed fine powder 2 mg into the spirulina fine powder 5.7 g, and evenly mixing the mixture to form *5 grains with equal weight, namely, forming the snacks which are eaten after the type E dinner and 10 minutes before sleep for the middle diabetics in the type II diabetics, wherein, the snacks have to be eaten at one time for non-fasting food therapy before the sleep with warmer water under 60 DEG. C.;

6. Adding the pumpkin fine powder 8.0 g, the balsam pear fine powder 14.6 mg and the lychee seed fine powder 2 mg into the spirulina fine powder 5.9 g, and evenly mixing the mixture to form *5 grains with equal weight, namely, forming the snacks which are eaten after the type F dinner and 10 minutes before sleep for the middle diabetics in the type II diabetics, wherein, the snacks have to be eaten at one time for non-fasting food therapy before the sleep with warmer water under 60 DEG. C.;

7. Adding the pumpkin fine powder 9.5 g, the balsam pear fine powder 14.7 mg and the lychee seed fine powder 2 mg into the spirulina fine powder 6.1 g, and evenly mixing the mixture to form *5 grains with equal weight, namely, forming the snacks which are eaten after the type G dinner and 10 minutes before sleep for the middle diabetics in the type II diabetics, wherein, the snacks have to be eaten at one time for non-fasting food therapy before the sleep with warmer water under 60 DEG. C.;
8. Adding the pumpkin fine powder 9.5 g, the balsam pear fine powder 14.8 mg and the lychee seed fine powder 2 mg into the spirulina fine powder 6.2 g, and evenly mixing the mixture to form *5 grains with equal weight, namely, forming the snacks which are eaten after the type H dinner and 10 minutes before sleep for the middle diabetics in the type II diabetics, wherein, the snacks have to be eaten at one time for non-fasting food therapy before the sleep with warmer water under 60 DEG. C.;
9. Adding the pumpkin fine powder 9.5 g, the balsam pear fine powder 14.9 mg and the lychee seed fine powder 2 mg into the spirulina fine powder 6.3 g, and evenly mixing the mixture to form *5 grains with equal weight, namely, forming the snacks which are eaten after the type J dinner and 10 minutes before sleep for the middle diabetics in the type II diabetics, wherein, the snacks have to be eaten at one time for non-fasting food therapy before the sleep with warmer water under 60 DEG. C.;

EXAMPLE 13

Aiming at the severe diabetics in the type II diabetics, the preparation, the dosage and the taking mode of special snacks which have to be eaten before sleep for balancing night blood sugar are prepared by dosing the qualifiedly prepared standard spirulina fine powder, the pumpkin fine powder, the balsam pear fine powder and the lychee seed fine powder under absolute sterile environment in the follows ways:
1. Adding the pumpkin fine powder 5.5 g, the balsam pear fine powder 15 mg and the lychee seed fine powder 2 mg into the spirulina fine powder 6.4 g, and evenly mixing the mixture to form *6 grains with equal weight, namely, forming the snacks which are eaten after the type A dinner and 10 minutes before sleep for the middle diabetics in the type II diabetics, wherein, the snacks have to be eaten at one time for non-fasting food therapy before the sleep with warmer water under 60 DEG. C.;
2. Adding the pumpkin fine powder 6.0 g, the balsam pear fine powder 15.1 mg and the lychee seed fine powder 2 mg into the spirulina fine powder 6.5 g, and evenly mixing the mixture to form *6 grains with equal weight, namely, forming the snacks which are eaten after the type B dinner and 10 minutes before sleep for the middle diabetics in the type II diabetics, wherein, the snacks have to be eaten at one time for non-fasting food therapy before the sleep with warmer water under 60 DEG. C.;
3. Adding the pumpkin fine powder 7.5 g, the balsam pear fine powder 15.2 mg and the lychee seed fine powder 2 mg into the spirulina fine powder 6.6 g, and evenly mixing the mixture to form *6 grains with equal weight, namely, forming the snacks which are eaten after the type C dinner and 10 minutes before sleep for the middle diabetics in the type II diabetics, wherein, the snacks have to be eaten at one time for non-fasting food therapy before the sleep with warmer water under 60 DEG. C.;
4. Adding the pumpkin fine powder 9.0 g, the balsam pear fine powder 15.3 mg and the lychee seed fine powder 2 mg into the spirulina fine powder 6.7 g, and evenly mixing the mixture to form *6 grains with equal weight, namely, forming the snacks which are eaten after the type D dinner and 10 minutes before sleep for the middle diabetics in the type II diabetics, wherein, the snacks have to be eaten at one time for non-fasting food therapy before the sleep with warmer water under 60 DEG. C.;
5. Adding the pumpkin fine powder 10.5 g, the balsam pear fine powder 15.4 mg and the lychee seed fine powder 2 mg into the spirulina fine powder 6.8 g, and evenly mixing the mixture to form *6 grains with equal weight, namely, forming the snacks which are eaten after the type E dinner and 10 minutes before sleep for the middle diabetics in the type II diabetics, wherein, the snacks have to be eaten at one time for non-fasting food therapy before the sleep with warmer water under 60 DEG. C.;
6. Adding the pumpkin fine powder 11.0 g, the balsam pear fine powder 15.5 mg and the lychee seed fine powder 2 mg into the spirulina fine powder 6.9 g, and evenly mixing the mixture to form *6 grains with equal weight, namely, forming the snacks which are eaten after the type F dinner and 10 minutes before sleep for the middle diabetics in the type II diabetics, wherein, the snacks have to be eaten at one time for non-fasting food therapy before the sleep with warmer water under 60 DEG. C.;
7. Adding the pumpkin fine powder 12.5 g, the balsam pear fine powder 15.6 mg and the lychee seed fine powder 2 mg into the spirulina fine powder 7.0 g, and evenly mixing the mixture to form *6 grains with equal weight, namely, forming the snacks which are eaten after the type G dinner and 10 minutes before sleep for the middle diabetics in the type II diabetics, wherein, the snacks have to be eaten at one time for non-fasting food therapy before the sleep with warmer water under 60 DEG. C.;
8. Adding the pumpkin fine powder 12.7 g, the balsam pear fine powder 15.7 mg and the lychee seed fine powder 2 mg into the spirulina fine powder 7.1 g, and evenly mixing the mixture to form *6 grains with equal weight, namely, forming the snacks which are eaten after the type H dinner and 10 minutes before sleep for the middle diabetics in the type II diabetics, wherein, the snacks have to be eaten at one time for non-fasting food therapy before the sleep with warmer water under 60 DEG. C.;
9. Adding the pumpkin fine powder 12.9 g, the balsam pear fine powder 15.8 mg and the lychee seed fine powder 2 mg into the spirulina fine powder 7.2 g, and evenly mixing the mixture to form *6 grains with equal weight, namely, forming the snacks which are eaten after the type J dinner and 10 minutes before sleep for the middle diabetics in the type II diabetics, wherein, the snacks have to be eaten at one time for non-fasting food therapy before the sleep with warmer water under 60 DEG. C.;

EXAMPLE 14

Aiming at the levis diabetics in the type II diabetics complicating with Hyperlipidemia and hyperpiesis, the preparation, the dosage and the taking mode of special snacks which have to be eaten before sleep at the morning, the noon and the night are prepared by dosing the qualifiedly prepared standard spirulina fine powder and the balsam pear fine powder under absolute sterile environment in the follows ways:
1. Adding the balsam pear fine powder 4 g into the spirulina fine powder 1.1 g, and evenly mixing the mixture to form 4 grains with equal weight or capsule with equal weight, namely, forming the snacks which are eaten before type A breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

2. Adding the balsam pear fine powder 4.3 g into the spirulina fine powder 1.2 g, and evenly mixing the mixture to form 4 grains with equal weight or capsule with equal weight, namely, forming the snacks which are eaten before type B breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

3. Adding the balsam pear fine powder 4.6 g into the spirulina fine powder 1.3 g, and evenly mixing the mixture to form 4 grains with equal weight or capsule with equal weight, namely, forming the snacks which are eaten before type C breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

4. Adding the balsam pear fine powder 4.9 g into the spirulina fine powder 1.4 g, and evenly mixing the mixture to form 4 grains with equal weight, namely, forming the snacks which are eaten before type D breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

5. Adding the balsam pear fine powder 5.2 g into the spirulina fine powder 1.5 g, and evenly mixing the mixture to form 4 grains with equal weight, namely, forming the snacks which are eaten before type E breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

6. Adding the balsam pear fine powder 5.5 g into the spirulina fine powder 1.4 g, and evenly mixing the mixture to form 4 grains with equal weight, namely, forming the snacks which are eaten before type F breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

7. Adding the balsam pear fine powder 5.8 g into the spirulina fine powder 1.7 g, and evenly mixing the mixture to form 4 grains with equal weight, namely, forming the snacks which are eaten before type G breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

8. Adding the balsam pear fine powder 6.0 g into the spirulina fine powder 1.8 g, and evenly mixing the mixture to form 4 grains with equal weight, namely, forming the snacks which are eaten before type H breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

9. Adding the balsam pear fine powder 6.1 g into the spirulina fine powder 1.9 g, and evenly mixing the mixture to form 4 grains with equal weight, namely, forming the snacks which are eaten before type J breakfast, lunch, dinner and 10 minutes before sleep at each day for the levis diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

EXAMPLE 15

Aiming at the middle diabetics in the type II diabetics complicating with Hyperlipidemia and hyperpiesis, the preparation, the dosage and the taking mode of special snacks which are eaten before sleep at the morning, the noon and the night are prepared by dosing the qualifiedly prepared standard spirulina fine powder and the balsam pear fine powder under absolute sterile environment in the follows ways:

1. Adding the balsam pear fine powder 4 g into the spirulina fine powder 1.1 g, and evenly mixing the mixture to form 5 grains with equal weight, namely, forming the snacks which are eaten before type A breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

2. Adding the balsam pear fine powder 6.3 g into the spirulina fine powder 2.1 g, and evenly mixing the mixture to form 5 grains with equal weight, namely, forming the snacks which are eaten before type B breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

3. Adding the balsam pear fine powder 6.4 g into the spirulina fine powder 2.2 g, and evenly mixing the mixture to form 5 grains with equal weight, namely, forming the snacks which are eaten before type C breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

4. Adding the balsam pear fine powder 6.5 g into the spirulina fine powder 2.3 g, and evenly mixing the mixture to form 5 grains with equal weight, namely, forming the snacks which are eaten before type D breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

5. Adding the balsam pear fine powder 6.6 g into the spirulina fine powder 2.4 g, and evenly mixing the mixture to form 5 grains with equal weight, namely, forming the snacks which are eaten before type E breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

6. Adding the balsam pear fine powder 6.7 g into the spirulina fine powder 2.5 g, and evenly mixing the mixture to form 5 grains with equal weight, namely, forming the snacks which are eaten before type F breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

7. Adding the balsam pear fine powder 6.8 g into the spirulina fine powder 2.6 g, and evenly mixing the mixture to form 5 grains with equal weight, namely, forming the snacks which are eaten before type G breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

8. Adding the balsam pear fine powder 6.9 g into the spirulina fine powder 2.7 g, and evenly mixing the mixture to form 5 grains with equal weight, namely, forming the snacks which are eaten before type H breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

9. Adding the balsam pear fine powder 7.0 g into the spirulina fine powder 2.8 g, and evenly mixing the mixture to form 5 grains with equal weight, namely, forming the snacks which are eaten before type J breakfast, lunch, dinner and 10 minutes before sleep at each day for the middle diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

EXAMPLE 16

Aiming at the severe diabetics in the type II diabetics complicating with Hyperlipidemia and hyperpiesis, the preparation, the dosage and the taking mode of special snacks which are eaten before sleep at the morning, the noon and the night are prepared by dosing the qualifiedly prepared standard spirulina fine powder and the balsam pear fine powder under absolute sterile environment in the follows ways:

1. Adding the balsam pear fine powder 7.1 g into the spirulina fine powder 2.9 g, and evenly mixing the mixture to form 6 grains with equal weight, namely, forming the snacks which are eaten before type A breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

2. Adding the balsam pear fine powder 7.2 g into the spirulina fine powder 3.0 g, and evenly mixing the mixture to form 6 grains with equal weight, namely, forming the snacks which are eaten before type B breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

3. Adding the balsam pear fine powder 7.3 g into the spirulina fine powder 3.1 g, and evenly mixing the mixture to form 6 grains with equal weight, namely, forming the snacks which are eaten before type C breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

4. Adding the balsam pear fine powder 7.4 g into the spirulina fine powder 3.2 g, and evenly mixing the mixture to form 6 grains with equal weight, namely, forming the snacks which are eaten before type D breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

5. Adding the balsam pear fine powder 7.5 g into the spirulina fine powder 3.3 g, and evenly mixing the mixture to form 6 grains with equal weight, namely, forming the snacks which are eaten before type E breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

6. Adding the balsam pear fine powder 7.6 g into the spirulina fine powder 3.4 g, and evenly mixing the mixture to form 6 grains with equal weight, namely, forming the snacks which are eaten before type F breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

7. Adding the balsam pear fine powder 7.7 g into the spirulina fine powder 3.5 g, and evenly mixing the mixture to form 6 grains with equal weight, namely, forming the snacks which are eaten before type G breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

8. Adding the balsam pear fine powder 7.8 g into the spirulina fine powder 3.6 g, and evenly mixing the mixture to form 6 grains with equal weight, namely, forming the snacks which are eaten before type H breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

9. Adding the balsam pear fine powder 7.9 g into the spirulina fine powder 3.7 g, and evenly mixing the mixture to form 6 grains with equal weight, namely, forming the snacks which are eaten before type J breakfast, lunch, dinner and 10 minutes before sleep at each day for the severe diabetics in the type II diabetics complicating with hyperlipidemia and hyperpiesis, wherein, the snacks which are used for reducing blood fat and blood pressure have to be eaten at one time for fasting food therapy with warmer water under 60 DEG. C.;

The prescription and the use of the present invention effectively reduce and stabilize the blood sugar concentration of the diabetics, avoid the complicating diseases of the diabetics, and ensure the health of the patients.

What is claimed is:

1. A composition for treating diabetes comprising the following active components based on the parts by weight:
   10-100 parts of Pumpkin powder;
   6-200 parts of spirulina;
   2-90 parts of Lychee Seed, and
   10-100 parts of balsam pear powder.

2. The composition of claim 1, wherein the composition comprises the following active components based on the parts by weight:
   10-60 parts of Pumpkin powder;
   6-80 parts of spirulina;
   2-60 parts of Lychee Seed; and
   10-60 parts of balsam pear powder.

3. A method for preparing a composition of claim 1 comprising the following active components based on the parts by weight, comprising steps of grinding and mixing the active components:
   10-100 parts of Pumpkin powder;
   6-200 parts of spirulina;
   2-90 parts of Lychee Seed, and
   10-100 parts of balsam pear powder.

4. The method of claim 3, wherein the composition comprises the following active components based on the parts by weight:
   10-60 parts of Pumpkin powder;
   6-80 parts of spirulina;
   2-60 parts of Lychee Seed; and
   10-60 parts of balsam pear powder.

5. A method for the treatment of diabetes in a patient, comprising the administration of an effective amount of a composition of claim 1 comprising the following active components based on the parts by weight:
   10-100 parts of Pumpkin powder;
   6-200 parts of spirulina;
   2-90 parts of Lychee Seed, and
   10-100 parts of balsam pear powder.

6. The method of claim 5, wherein the composition comprises the following active components based on the parts by weight:
   10-60 parts of Pumpkin powder;
   6-80 parts of spirulina;
   2-60 parts of Lychee Seed; and
   10-60 parts of balsam pear powder.

* * * * *